United States Patent
Strassl et al.

(10) Patent No.: US 6,822,186 B2
(45) Date of Patent: Nov. 23, 2004

(54) LASER PROCESSING APPARATUS FOR PLASMA-INDUCED ABLATION

(75) Inventors: Martin Strassl, Bürmoos (AT); Harald Schörghofer, Bürmoos (AT); Anton Kassenbacher, Traunstein (DE)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 39 days.

(21) Appl. No.: 10/439,974

(22) Filed: May 16, 2003

(65) Prior Publication Data

US 2003/0226831 A1 Dec. 11, 2003

(30) Foreign Application Priority Data

May 17, 2002 (DE) .......................................... 102 22 117

(51) Int. Cl.⁷ .............................................. B23K 26/36
(52) U.S. Cl. ............................. 219/121.62; 219/121.68
(58) Field of Search ...................... 219/121.61, 121.62, 219/121.67, 121.68, 121.69, 121.7, 121.71, 121.72, 121.83

(56) References Cited

U.S. PATENT DOCUMENTS

| | | | | |
|---|---|---|---|---|
| 5,272,312 A | * | 12/1993 | Jurca ...................... | 219/121.83 |
| 5,486,677 A | * | 1/1996 | Maischner et al. .... | 219/121.83 |
| 6,215,094 B1 | * | 4/2001 | Dausinger et al. ..... | 219/121.62 |

* cited by examiner

Primary Examiner—Samuel M. Heinrich
(74) Attorney, Agent, or Firm—Leonard J. Santisi; Frommer Lawrence & Haug LLP (57) ABSTRACT

The present invention relates to a laser processing apparatus for plasma-induced ablation having a laser light source for generating a processing laser beam, a focussing means for focussing the processing laser beam and an optical detection device for detecting the plasma radiation generated during an ablation, in which case the laser processing apparatus comprises an evaluation and/or control unit, the optical detection device being designed in such a way that it can output to the evaluation and/or control unit a signal dependent on the intensity of the detected plasma radiation, and the laser processing apparatus is designed in such a way that it can automatically be switched from a processing mode into a quiescent mode and/or from the quiescent mode into the processing mode, in a manner dependent on said signal.

13 Claims, 4 Drawing Sheets

LASER PROCESSING APPARATUS FOR PLASMA-INDUCED ABLATION

The invention relates to a laser processing apparatus in particular a medical laser processing apparatus, for plasma-induced ablation, which comprises a laser light source for generating a processing laser beam, a focussing means for focussing the processing laser beam and an optical detection device for detecting the plasma radiation generated during an ablation.

Such laser processing apparatuses are used in different areas and for different purposes in diverse forms. They are used in particular in the medical field, primarily in dentistry, where they are used instead of a mechanical drill for the ablation or removal of tooth material, in particular carious tooth material.

In contrast to mechanical drill devices, in which a contact between the processing device and the region to be worked is always prescribed for removal purposes, in the case of the laser processing apparatuses which enable contactless processing and removal, the correct positioning or the correct processing distance with respect to the material to be processed is of major importance.

Therefore, it has been proposed in the prior art to equip such laser processing apparatuses, in particular handpieces for such laser processing apparatuses, with a device for distance measurement.

The German patent application (official file reference 100 42 220.9) describes a handpiece for a laser processing apparatus which is provided with a distance measuring device which monitors the distance between a handpiece and the material to be processed. The distance measuring device proposed is a proximity sensor, for example an ultrasonic sensor, for contactlessly measuring the required distance or a mechanical distance pin which is fitted to the handpiece in the vicinity of the region to be processed and to the handpiece preferably in the direction of the emerging laser light.

However, such distance measuring devices are in part complex and costly and in some instances susceptible to faults and make the laser processing apparatus more expensive.

Therefore, it is an object of the present invention to provide a laser processing apparatus which enables a cost-effective and largely fault-unsusceptible ablation of a material and, in particular, satisfies very stringent safety requirements during the operation of the apparatus and precludes endangerment of the patient and/or also of the user or the operator of such a laser processing apparatus or, if appropriate, also of third parties.

This object is achieved by means of a laser processing apparatus according to claim 1; claims 2 to 13 relate to particularly advantageous embodiments of the laser processing apparatus according to the invention.

According to the invention, the laser processing apparatus comprises a laser light source for generating a processing laser beam, a focussing means for focussing the processing laser beam and an optical detection device for detecting the plasma radiation generated during the ablation of the material, the laser processing apparatus furthermore comprising an evaluation and/or a control unit, which are designed in such a way that it automatically switches the laser processing apparatus from a processing mode into a quiescent mode of the laser processing apparatus or of the laser light source and/or vice versa in a manner dependent on the values for the intensity of the plasma radiation which are determined by the detection device.

The invention has the advantage that it is not necessary for the distance to be measured by means of an additional distance measuring device; by contrast, it is possible to ensure that the correct distance or the desired distance range is complied with merely by monitoring the plasma radiation which arises during the ablation or the removal of the material to be processed. By way of example, if the laser processing apparatus is not operated correctly by the operator, e.g. by virtue of a dental handpiece of such a laser processing apparatus being held in such a way that the distance between the handpiece and the material to be processed becomes too large or too small, the excessively low power density or the excessively low fluence at the material to be processed means that no plasma-induced ablation and therefore no plasma radiation arises or the intensity of the plasma decreases at least to a very great extent, so that, from monitoring the plasma radiation alone, it is possible to draw the desired conclusions with regard to the correct distance from the material to be processed.

In the case, moreover, where an operator holds the laser processing apparatus or a corresponding handpiece in such a way that an emitted laser processing beam does not impinge on the material to be processed, which can lead to endangerment of the patient, no plasma radiation is detected and the laser processing apparatus is automatically put into a quiescent mode, thus enabling a secure and hazard-free treatment.

It shall be pointed out at this juncture that the intensity of the plasma can be measured essentially independently of wavelength, in particular can be measured over the entire wavelength range. However, it is also possible for the intensity to be measured only in a specific selected wavelength range or in a plurality of wavelength ranges, which can preferably be chosen depending on the area of application, or else only at one or a plurality of specific wavelengths.

The values determined by the optical detection device are preferably forwarded to the evaluation and/or control unit in the form of a signal, the evaluation unit regarding a sharp drop in the intensity of the plasma radiation, if appropriate a drop down to 0, as an indicator of the fact that the material to be processed is no longer situated in the region of the focus or of a predetermined depth of field range and the desired distances between, for example, a handpiece and the area to be processed or the material to be processed are therefore not being complied with, so that effective or secure processing is longer ensured.

In this case, according to the invention, the evaluation and/or control unit are designed in such a way that they automatically switch the laser processing apparatus or the laser light source back and forth between a processing mode and a quiescent mode in a manner dependent on the values determined by the optical detection device and the corresponding signal generated by the detection device. It can thus be ensured that the laser processing apparatus is switched into a quiescent mode in the event of a processing or treatment in which the required distances are not complied with, which leads to a change in the intensity of the plasma radiation or a complete extinction of the plasma.

The laser processing apparatus according to the invention thus ensures, in a simple and cost-effective manner, that the laser processing apparatus is in a processing mode and a laser processing beam can be emitted only when the correct and desired distances for processing or for treatment are complied with, and an effective and secure processing or treatment is therefore ensured. Therefore, in the case of a laser processing apparatus according to the invention, it is possible to dispense with a distance monitoring device, it being ensured at the same time, however, that the laser processing apparatus or the laser light source does not emit a processing laser beam unless a plasma-induced ablation is also brought about by the latter.

Emission of a processing laser beam without a plasma-induced ablation must be avoided in particular because the energy radiated in by the laser, if it does not lead to the desired ablation, may lead in particular to heating of the material being irradiated, which can lead to undesired damaged to the material or to injuries. The laser processing apparatus according to the invention therefore ensures, in a simple and cost-effective and also a reliable manner, that a laser power is output only when it also actually leads, as desired, to the plasma-induced ablation.

The optical detection device may be a photodetector or else a spectrometer, but it is also possible to provide other sensors which can evaluate the intensity of an illumination, either in a defined wavelength range, in a wavelength-specific manner or in a wavelength-nonspecific manner.

In a preferred embodiment, the evaluation and/or the control unit are designed as an integral component, the evaluation and/or the control unit being realized in particular by a microcomputer. However, it is also possible for evaluation unit and control unit to be mutually separate units or components.

In a particularly preferred embodiment of the laser processing apparatus, the evaluation unit and/or the control unit are designed in such a way that the laser processing apparatus is automatically switched from a processing mode into a quiescent mode if the intensity of the plasma radiation detected by the detection device falls below a fixed first threshold value. This first threshold value is preferably a very low value; in particular, the first threshold value may be 0 or just above a value of 0, so that possible "noise" of the optical detection device and/or of the evaluation unit and/or of the control unit is encompassed. Preferably, a first threshold value is from 10% to 50% above the value of a so-called "dark measurement", i.e. a measurement of the light intensity of the region to be processed without emission of a processing laser beam. Such a dark measurement is preferably carried out automatically by the laser processing apparatus before switching into an operating mode, so that an absolute value for the first threshold value can automatically be defined when prescribing the corresponding relative values (of the first threshold value with regard to the "dark value").

The relative values for the first threshold value are preferably adjustable; in particular, the first threshold value may also be significantly higher, for example between 100% and 300% above the value of the corresponding dark measurement.

It may be provided that a dark measurement is carried out at regular intervals and the first threshold value is regularly updated as a result; it is also possible for the laser processing apparatus to be designed in such a way that an average value of the last three dark measurements is in each case used as reference value for the first threshold value, that is to say as value for the dark measurement.

In a further preferred embodiment of the laser processing apparatus according to the invention, the evaluation unit and/or the control unit are designed in such a way that the laser processing apparatus can furthermore be operated in a so-called trial mode, preferably in a temporally very narrowly limited trial mode, which may be regarded as part of the quiescent mode or lies within said quiescent mode. During the trial mode, although the laser processing apparatus is not in the actual operating mode, a processing laser beam is emitted on a trial basis and in a temporally restricted manner, in particular in order to check whether the medical laser treatment apparatus or a handpiece or angle member is situated in the correct position for processing. If the processing laser beam emitted during the quiescent mode generates a plasma and if the intensity of this plasma radiation which is detected by the optical detection device at a specific measurement time lies above a definable second threshold value, then the laser processing apparatus is preferably automatically switched into the processing mode. Such a trial mode may be provided when a processing is initially started; however, it is also possible for the laser processing apparatus to run through a trial mode after the laser processing apparatus was switched, during the processing, from the processing mode automatically into a quiescent mode because the detected intensity of the plasma radiation was too low.

In a specific embodiment of the laser processing apparatus according to the invention, it is possible for the second threshold value to correspond to the first threshold value, but the second threshold value preferably lies above the first threshold value (preferably 10% to 30%, if appropriate even 50% to 80%, above the first threshold value), so that a hysteresis is produced.

The laser processing apparatus preferably furthermore comprises an activation device, which can be actuated by a user and is designed in such a way that it puts the laser processing apparatus into the quiescent mode if it is not actuated by the user. It is thus ensured that a processing laser beam is emitted only when the user actively desires processing. Therefore, a processing laser beam is emitted only when, on the one hand, the activation device is actuated by the user and, on the other hand, values for the intensity of the plasma radiation which lie within a previously defined range are supplied by the optical detection device. If one of these conditions is not met, the laser processing apparatus or the laser light source is in a quiescent mode.

In particular when a user-actuable activation device is provided, the laser processing apparatus is preferably designed in such a way that each time the activation device is actuated anew by the user, a dark measurement is automatically carried out first, so that the first and, if appropriate, the second threshold value are automatically defined.

It shall be pointed out at this juncture that the term "quiescent mode" of the laser processing apparatus or the laser light source can mean, on the one hand, that the laser light source is switched off, in other words no processing laser beam whatsoever is generated; however, it is also possible for the laser light source itself not to be switched off, but for the processing laser beam generated by the laser light source to be shielded, for example by means of a shutter. In the "processing mode", the processing laser beam is always generated and is not shielded either, so that a laser beam is emitted.

Shielding of the laser light source, for example by means of a shutter, is preferred particularly when a laser light source is used which requires a certain period of time to ensure stable emission of a laser light, this being the case in particular with pulsed laser light sources with short and high-energy laser pulses in the femtoseconds range.

The laser processing apparatus preferably comprises a delay device, which can be designed or set in variable fashion.

The delay device is preferably designed or set in such a way that, in the case where the intensity of the plasma radiation falls below a defined first threshold value (or when switching on the laser processing apparatus or when actuating an activation device), the quiescent mode is switched off only after a defined delay time $t_1$ or after a defined number x of pulses. What is thus made possible is that, in the event of, if appropriate, very short deviations from the desired processing conditions, the processing mode of the laser processing apparatus is maintained, thereby enabling continuous processing if the very short deviations from the desired conditions do not, for example, endanger the patient to be treated.

In a second realization, as an alternative or in addition, the delay device may be designed or set in such a way that, after an automatic changeover of the laser processing apparatus from a processing mode into a quiescent mode, the laser processing apparatus is automatically switched into the processing mode again, at least for a short period of time, after a defined time period $t_2$. What is thus made possible is that the processing is continued or resumed if the desired conditions were not complied with only for a specific period of time, without a user of the laser processing apparatus, for example a treating physician, having to take further measures. However, a processing is continued or resumed only when the activation device is actuated by the user or the laser processing apparatus is actively switched on or actuated by the user through a different measure.

Instead of the defined time $t_2$, it is also possible in this case to define a specific number y of pulses, for example if the laser light sources is not switched off, but rather only shielded.

In a further alternative or additional refinement, it is provided that the delay device is designed or set in such a way that the laser processing apparatus is switched into the operating mode again only for a defined time period $t_3$ or a defined number z of pulses it being changed over into the quiescent mode again after said time $t_3$ or after the z pulses unless the optical detection device forwards to the evaluation and/or control unit an intensity of a plasma radiation or corresponding signals which allow the conclusion to be drawn that the desired conditions are re-established.

If said defined intensity of the plasma radiation is not reached within the time period $t_3$ or within the z pulses generated, a changeover is made to the quiescent mode again.

In a further embodiment, this method can then be carried out anew, for example after a time $t_2$ or after y pulses. In a particular preferred embodiment, however, this method is carried out only over a defined number of repetitions, in which case, by way of example, after a number of 3 to 5 repetitions, an automatic changeover to the processing mode is no longer effected, in particular the processing can only be started again by means of, for example, a deactivation and renewed actuation of the activation device by the user.

In a preferred embodiment, both the threshold values and the fluence of the laser processing beam are adjustable, so that the laser processing apparatus can be set to the desired situation in a flexible manner. The predetermined time periods $t_1$, $t_2$ and $t_3$ preferably lie in a range of between 20 $\mu s$ and 100 ms, in particular in a range of from 0.1 to 10 ms, preferably in a range of from 1 ms to 5 ms. For the time period $t_3$, in particular, it is preferably the case that very short time periods are defined, in particular in a range below 1 ms. A time period $t_3 \leq 500$ $\mu s$ is preferably chosen, in particular in a range of between 10 $\mu s$ and 300 $\mu s$, in particular approximately 100 $\mu s$.

Instead of the time periods $t_1$ $t_2$ and $t_3$, it is also possible to define a specific number x, y and z of pulses, preferred values for the number x, y and z of pulses lying between 1 and 100, in particular in the range of from 5 to 30. A particularly preferred value is 10 pulses. It is also the case when defining the number of pulses that, in a preferred embodiment, in particular the number z of pulses can be chosen to be very low, a value which does not exceed 10 preferably being chosen for z, in particular z lying between 1 and 5 pulses.

In a particularly preferred embodiment, the laser processing apparatus furthermore comprises a synchronizing device by means of which the optical detection device for detecting the plasma radiation generated during an ablation, on the one hand, and the evaluation and/or control unit and the laser light source on the other hand, are adapted to one another. Such a synchronizing device is of importance particularly in the case of laser light sources which can also emit a pulsed processing laser beam, in which case it shall be pointed out at this juncture that the laser processing apparatus is suitable in particular precisely for such pulsed laser light sources and the system according to the invention exhibits its significant advantages precisely in the case of such pulsed laser light sources. In this connection, it shall also be pointed out again that the provision of the evaluation and/or control unit according to the invention and the control of the laser processing apparatus which is thus made possible is of extreme importance particularly in the case of high-energy pulsed laser systems, since, in the case where laser pulses are radiated at material without igniting a plasma, which, as explained, occurs particularly if a handpiece or a similar element of the laser processing apparatus is positioned incorrectly, the high-energy laser pulses can penetrate to an undesirable depth, for example into a tooth material, where they may lead to heating of the material. Thus, by way of example, if ignition of a plasma does not take place, such a laser pulse may penetrate several millimeters into the hard tooth substance, as a result of which the pulp can be irreversibly damaged by heating.

Such "incorrect operation" of the apparatus is automatically avoided as a result of the laser processing apparatus being put automatically into the quiescent mode, thereby ensuring reliable and safe treatment with such high-energy laser systems.

Since the plasma generated by the ablation also "pulsates" in the case of a pulsed processing laser beam, the points in time or time ranges at which the plasma can actually only occur must also be taken into account, the synchronizing device performing this coordination. The pulsating plasma radiation that is likewise produced, also called a plasma torch pulsates essentially with a repetition rate which corresponds to a pulse repetition rate f of the processing laser beam or the laser light source, the plasma radiation being generated for different lengths of time depending on the pulse duration t of the pulsating processing laser beam.

Therefore, between the emitted pulses of the processing laser beam, so-called "dark pauses" occur in which no plasma light can occur since no laser energy is being radiated either. The synchronizing device therefore coordinates the laser processing apparatus with regard to the pulse repetition rate f and, if appropriate, also to the pulse duration t of the laser light source or the processing laser beam, so that the pulse repetition rate f and the pulse duration t are used as characteristic quantities for the synchronizing device and thus for the control and coordination of the laser processing apparatus.

In a preferred embodiment, the pulse repetition frequency f and the pulse duration t and/or the temporal profile of the pulses of the synchronizing device are provided directly by the laser light source, including a so-called "start point", that is to say a first occurrence or starting of pulsed operation. In a further embodiment, however, it is also possible for the first occurrence of a plasma event to be chosen as the start point for the time measurement; furthermore, it is also possible for the first two or three plasma events to be used in order automatically to determine not only the start point but also the pulse durations t and the pulse repetition frequency or the repetition rate f. It is also possible for specific characteristic values of the laser light source to be stored and used with the first plasma events for the further coordination of the synchronizing device and the laser processing apparatus.

In a further embodiment, it is possible for each emitted pulse to be tapped off at the laser light source and used as a trigger for the optical detection device, thereby making it possible to register the occurrence of plasma on account of a pulse in real time.

In this way, it is possible to ensure in a simple and cost-effective manner that correct monitoring and control of the operation is possible even in the case of a laser processing apparatus which can generate a pulsed processing laser beam.

It shall be pointed out at this juncture that it is possible, in principle, for the plasma radiation generated to be measured essentially over the entire pulse period $\Delta t = 1/f$, in which case, of course, the time ranges in which no plasma can be produced for lack of energy being radiated in are not taken into account in the signal generation and for the control of the laser processing apparatus, or are correspondingly concomitantly taken into account in the case of a determination of an average value for the detected intensity over a specific measurement time period, which is likewise possible in the context of the invention, or the threshold value or values for the average value of the intensity have to be correspondingly lowered in a manner dependent on the so-called "dark phases". In a particular embodiment, however, the plasma radiation generated is taken into account only in a time period which is shorter than the pulse period $\Delta t$, in particular the time periods in which the plasma torch is generated or in which the plasma torch is extinguished and in which, therefore, particular intensity fluctuations occur not being taken into account. In a particular embodiment, the plasma radiation generated is only measured over a time period $\tau$ which is shorter than the pulse period $\Delta t$, where $\tau$, depending on the pulse duration t, may preferably be between 50 $\mu$s and 100 $\mu$s, preferably above 50 ps up to 100 ns, but the pulse period $\Delta t$, depending on the repetition rate f, may in this case preferably lie between 20 $\mu$s and 1 ms, in a further preferred embodiment between 2 $\mu$s and 50 $\mu$s, preferably below 35 $\mu$s. In the case of ultrashort laser pulses, in particular, the pulse duration t of the processing laser beam is generally shorter than the total lifetime of the plasma produced by the radiated-in energy; in this case, the plasma may even have a total duration which is up to 100 times or even longer than the pulse duration itself.

In one embodiment, the optical detection device detects the generated plasma radiation only during the desired time ranges; however, it is preferred for the optical detection device to continuously monitor the intensity of a plasma radiation that is possibly generated, but for the intensities determined by the optical detection device to be used only in the desired time periods for the further control of the laser processing apparatus.

Preferably, the laser processing apparatus furthermore comprises a device for generating a pilot laser beam, which may serve, in particular, for positioning a handpiece of the laser processing apparatus or a corresponding device. The pilot laser preferably generates a visible laser beam; in particular, semiconductor diodes are preferably used for generating a pilot laser beam.

In a particularly preferred embodiment, the device for generating a pilot laser beam is designed in such a way that the pilot laser beam has different emission wavelengths, so that the pilot laser beam can be changed over from red to green, for example.

It is preferred for the laser processing apparatus furthermore to comprise a device for optical, acoustic and/or tactile indication of the mode of the laser processing apparatus, so that additional information can be given to the operator, in particular a treating physician, during the treatment. Such a device may, in particular, be coupled to the abovementioned device for generating a pilot laser beam or be realized by said device, in which case, by way of example, a pilot laser beam of a first wavelength (for example in the red region) is emitted if the laser processing apparatus is in the quiescent mode, and a pilot laser beam of a second wavelength (for example in the green region) is emitted if the laser processing apparatus is in a processing mode.

It goes without saying that all other wavelengths are also conceivable in addition to the wavelengths in the red and green wavelength ranges mentioned above merely by way of example. It is preferred for the wavelength for the pilot laser beam to be chosen such that it as far as possible does not influence the measurement of the intensity of the plasma radiation. Conversely, it is also possible for the wavelengths or the wavelength range or ranges used for the measurement of the intensity of the plasma to be correspondingly adapted to the wavelength or wavelengths of the pilot laser beam. By way of example, it is possible to select only those wavelength ranges for the measurement of the intensity which lie outside the wavelength of the pilot laser beam. Since the wavelength of a pilot laser beam is limited to a very great extent, it is also possible to measure the intensity of the plasma radiation essentially over the entire wavelength range, but merely not to take account of the narrow wavelength range in which the pilot laser or lasers radiates or radiate for the measurement. This can also be done, for example, simply by placing a wavelength filter upstream of the optical detection device, which filter filters out precisely the wavelength of the pilot laser beam.

In the case of a laser light source which generates a pulsed laser light, typical pulse repetition rates f typically lie in a range of between 1 kHz and 50 kHz, while typical pulse durations t lie in the picoseconds or femtoseconds range.

If the laser light source operates with a pulse repetition rate f, then the optical detection device can detect a plasma radiation in each case at points in time or time ranges with an interval $\Delta t_{meas} = 1/f$. In this connection, it shall again be pointed out that the plasma lifetime may lie between 100 ps and 1 ns in the case of laser pulses $\leq 1$ ps. If the plasma detector is triggered in response to an output signal of the laser, then the laser processing apparatus can be put into the quiescent mode after the failure of just a single plasma torch to appear. In this case, the time interval $\Delta t_{meas}$ is between 10 s and 1 $\mu$s, in particular 20 $\mu$s given a repetition rate of 50 kHz, in particular 1 ms given a repetition rate of 1 kHz, in particular 33 $\mu$s given a repetition rate of 30 kHz, in particular 100 $\mu$s given a repetition rate of 10 kHz, and in particular 67 $\mu$s given a repetition rate of 15 kHz.

As has already been indicated in the handwritten documents, it shall be pointed out at this juncture that although it is preferred, as described above, for the optical detection device to measure in each case at points in time or time ranges with an interval which is directly coordinated with the pulse repetition frequency of a pulsed laser light source, it is also possible for the time interval $\Delta t_{meas}$ to be greater than 1/f and for the interval between two points in time or time ranges to be greater than the interval between two successive pulses. In particular, the interval may amount to a multiple of the intervals of the laser pulses, so that only every second, third or, to put it more generally, every nth pulse is taken into account. This makes it possible also to use inexpensive control systems that are not as fast. A further possibility for adapting the time interval $\Delta t_{meas}$ to a pulsed laser light source with a pulse repetition frequency f would therefore be in accordance with the formula $\Delta t_{meas}=a*1/f$, where a is a natural number.

A detection repetition rate or control repetition rate f, may therefore correspond to the pulse repetition rate f, but may also differ from the pulse repetition rate f; in particular, the pulse repetition rate f may be a multiple of the detection repetition rate f', so that f=a*f' holds true.

Consequently, for the evaluation, in the evaluation unit, in addition to the detected brightness value, the temporal sequence of the arriving signals is also compared with the pulse repetition rate f tapped off at the laser, in which case, however, the start point for the measurement does not have to coincide with the start point for the pulse, but rather can be chosen essentially freely in the pulse interval $\Delta t$. In this case, the start point for the measurement is preferably chosen such that the plasma already formed is optimally detected. The start point for the measurement preferably lies in the time period in which a laser pulse impinges on the material to be processed, or shortly afterward, that is to say while a plasma still exists, but it is also possible, in principle, for the start point for the measurement to lie within a so-called dark phase. It is thus possible to ascertain in an extremely simple manner whether or not a plasma has actually been ignited per pulse.

In a further preferred embodiment, it is also possible to choose the first occurrence of a plasma event as the start point of the time measurement and to interrogate the pulse pauses by means of a table stored in the evaluation unit and to compare them with the brightness values occurring after these times. In yet another preferred embodiment, each emitted pulse is tapped off at the laser and used as a trigger for the brightness measurement, thereby making it possible to register the occurrence of plasma on account of a pulse in real time.

In accordance with a further aspect, the laser processing apparatus comprises a device for generating a distance indicator as optical auxiliary means for the user. Such a device for generating a distance indicator is not comparable to range finding since merely the fact of whether or not the user is at the correct distance is indicated or specified to said user, for example by means of optical projections. Such a device for generating a distance indicator serves, in particular, for giving the user of the laser processing apparatus further expedient information for the handling of, for example, a handpiece of a laser treatment apparatus.

Such a device for generating a distance indicator preferably comprises a projection device for projecting a crosshair in the focal region of the processing laser beam, in which case, in the event of a deviation in the processing distance, i.e. in the case where the focus of the processing laser beam does not lie at the level of the material to be processed, the bars of the crosshair move or shift apart on account of the projection.

Such a projection device may also be combined with the abovementioned device for generating a pilot laser beam and/or a device for the optical, acoustic and/or tactile indication of the mode of the laser processing apparatus.

Figure 1:
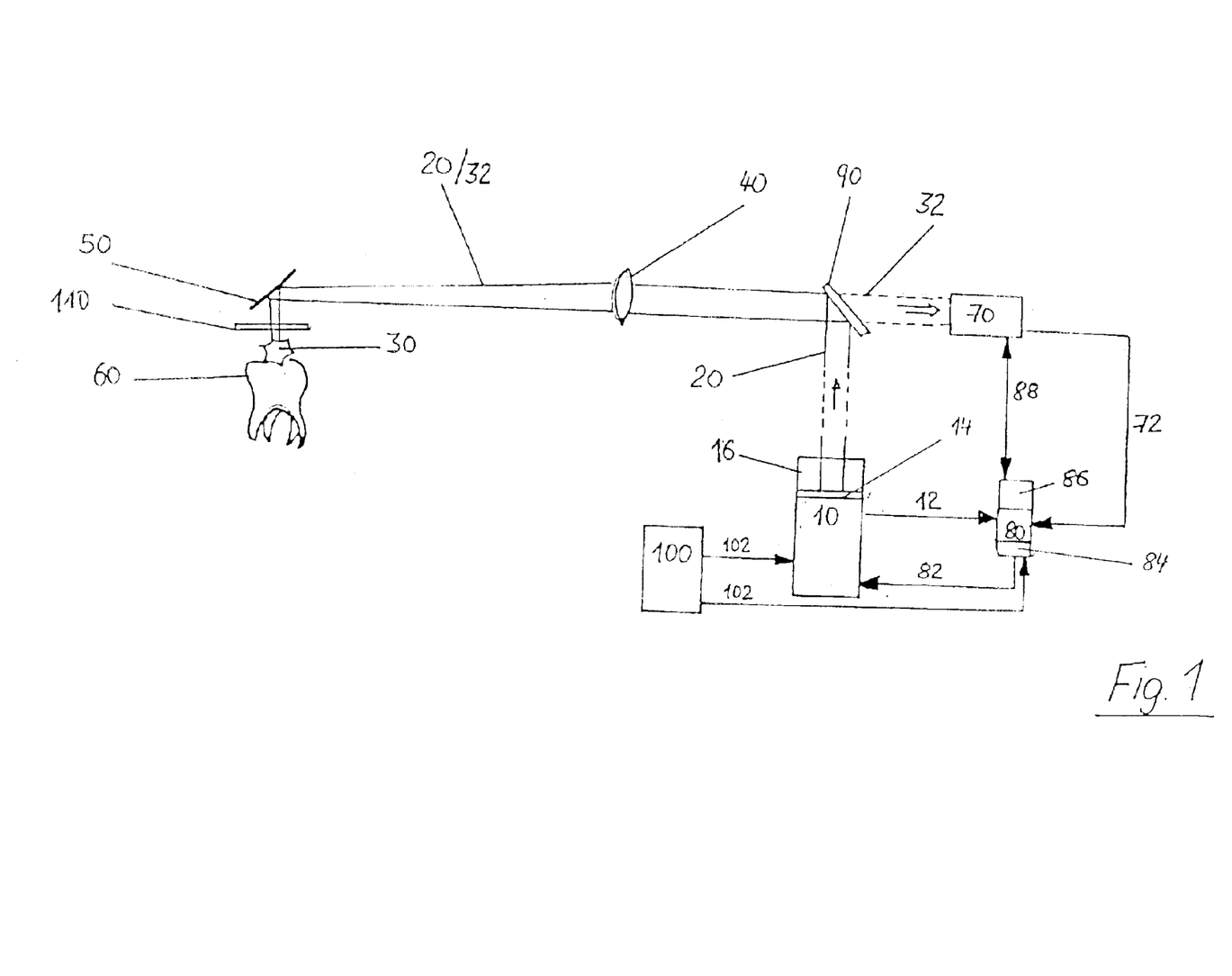
FIG. 1 shows a construction of an embodiment of a laser processing apparatus according to the invention.

These and further features and advantages of the invention will become even more apparent from the schematic illustrations below, in which:

FIG. 1 shows, schematically and for the purpose of elucidating the principle, some components of an embodiment of a laser processing apparatus according to the invention, which is used to carry out a plasma-induced ablation, here on a tooth.

The embodiment shown in FIG. 1 comprises a laser light source 10, in this case a laser light source which can generate a processing laser beam 20, which is pulsed. The laser light source 10 of this embodiment is designed in such a way that it can be switched between a pulsed operating mode and a cw operating mode (continuous wave operating mode).

In the embodiment shown here, a Yb:KGW laser is used, but it is also possible to use e.g. a Yb:YAG laser, Nd:YAG laser, a fiber laser or other known laser light sources. Laser light sources which can generate ultrashort laser pulses (USLP) are preferably used, since these are particularly well suited to the plasma-induced ablation. The pulse lengths t may lie in the picoseconds range and preferably even lie in the femtoseconds range.

In its beam course in the case of the embodiment shown in FIG. 1, the processing laser beam 20 emitted by the laser light source 10 firstly impinges on a beam splitter 90, which acts as a reflective mirror for the wavelength of the processing laser beam 20, so that the processing laser beam 20 is deflected approximately by 90° and passes through a focussing lens 40. Only one focussing lens 40 is illustrated in FIG. 1, but it shall be understood that generally provision is made of a plurality of optical elements for the focussing and/or also partial expansion or generally for the influencing of the processing laser beam 20. The illustration of further optical elements has been dispensed with in FIG. 1, however, for reasons of clarity.

The processing laser beam 20 subsequently impinges on a reflective mirror 50, which directs the processing laser beam 20 onto a material to be processed, in this case a tooth 60.

It shall be pointed out at this juncture that, in particular, the focussing lens 40, and, if appropriate, further optical elements, as explained above, and the mirror 50 are provided in a handpiece (not shown) of the laser processing apparatus, provided on the processing side. The arrangement with the reflective mirror 50 as shown in FIG. 1 is suitable in particular for handpieces and angle members in which the processing laser beam 20 is emitted at an angle of about 90° to a longitudinal axis of an angle member, since this enables better handling and accessibility particularly for dentistry.

The processing laser beam 20 impinges on the tooth 60 to be processed, so that the plasma-induced ablation of the tooth material takes place and a plasma 30 is generated.

The plasma radiation 32 generated by the plasma 30 or the plasma light traverses, at least in part, essentially the beam path of the processing laser beam 20, as has been described above, in other words is reflected from the mirror 50, passes through the focussing lens 40 and, if appropriate, further optical elements (not shown here) and impinges on the beam splitter 90, which, however, is transmissive for the wavelength range of the plasma radiation 32, so that the plasma radiation 32 is fed to an optical detection device 70. In this embodiment, a simple photodetector which measures the intensity of the plasma radiation is provided as the optical detection device 70. However, it is also possible to use more complex systems as the optical detection device, in particular optical detection devices which evaluate the plasma radiation 32 in a wavelength-selective manner. By way of example, a spectrometer may be used as the optical detection device. It is also possible, in principle, to use for example a CCD camera (charge coupled device camera) or a CMOS image sensor (complementary metal oxide semiconductor image sensor) as the optical detection device or as part of an optical detection device.

The values for the plasma radiation 32 which are determined by the optical detection device 70, which may also be referred to as a sensor, are converted into a signal 72 and fed to a combined evaluation and control unit 80, the evaluation and control unit 80 being a computer system in this embodiment. However, all other open-loop and closed-loop control systems are also conceivable, in principle, such as e.g. SPC (stored-program controllers), microcontrollers or analog control loops.

Furthermore, a signal 12 is fed to the evaluation and control unit 80 from the laser light source 10, which signal outputs data about the operating state of the laser light source 10 to the evaluation and control unit 80. Depending on the values determined by the optical detection device 70 and on the signal 72, the evaluation and control unit 80 outputs a control signal 82, which is fed to the laser light source 10 and thus controls the laser light source 10, in particular switches the laser light source 10 from a quiescent mode to a processing mode, and vice versa. However, it is also possible for the evaluation and control unit 80 not only to switch the laser light source to a quiescent mode or to a processing mode, but also, furthermore, to perform controls of the laser light source depending on the information fed to it, for example to control a pulse duration t or a pulse repetition frequency f, or else to control the radiated power of the laser light source or other characteristic values.

In this embodiment, a delay device 84 is integrated in the evaluation and control unit 80. Furthermore, the embodiment of the laser processing apparatus as shown in FIG. 1 comprises an activation device 100, by means of which a user, in particular a treating physician, can specify when, in principle, he wishes processing, i.e. the emission of a processing laser beam 20. This activation device 100 is advantageously designed in the form of a foot-operated switch which can be actuated by the operator of the processing laser device. A signal 102, which specifies whether the activation device is activated or deactivated, or actuated or not actuated, by the user, is forwarded to the laser light source 10 and/or the evaluation and control unit 80, preferably, as in this embodiment, both to the laser light source 10 and to the combined evaluation and control unit 80, which is provided with a delay device 84.

Furthermore, the evaluation and control unit 80 comprises a synchronizing device 86, by means of which the laser processing apparatus and, in particular, the optical detection device and also the evaluation and control unit 80 are coordinated with the particular characteristic of the processing laser beam, a pulse repetition frequency f and a measurement interval $\Delta t_{meas}$—dependent on the pulse interval 1/f—of a pulsed processing laser beam being taken into account, in particular, in the coordination. The provision of said synchronizing device 86 ensures that the intensity of the plasma radiation 32 detected or determined by the optical detection device 70 is taken into account only when energy is actually emitted from the laser light source to the tooth 60 to be treated here, that is to say in the time periods in which a pulse impinges on the region of the material to be processed, so that an ablation can actually take place and a plasma light or a plasma torch can be generated, while no energy is transmitted to the tooth 60 in the time ranges between two successive pulses, so that no plasma torch can be generated either.

A typical operation of the laser processing apparatus shown in FIG. 1 may proceed for example as follows: an operator of the laser treatment apparatus, in particular a treating physician, guides a handpiece (not shown here), which, as explained above, comprises in particular the focussing lens 40 and the mirror 50, into the vicinity of a tooth 60, so that the handpiece is brought to a desired position for the processing. Afterward, the operator actuates the activation device 100 and a corresponding signal 102 is passed to the evaluation and control unit 80 and to the laser light source 10. The evaluation and control unit 80, which furthermore receives the signal 72 from the optical detection device 70 which signal indicates that, since the processing has not yet started, the intensity of the plasma radiation is equal to 0 since no plasma is ignited, therefore generates a control signal 82 which is fed to the laser light source 10.

The control signal 82 has the effect that a processing laser beam 20 is generated for a predetermined time period $t_2$. This defined time period $t_2$ is variable and can be input via the evaluation and control unit 80. The time period $t_2$ preferably lies in a range of from 20 µs to 100 ms, and is 1 ms in the case depicted here.

Instead of a defined time period $t_2$, in the case of a pulsed processing laser beam 20, it is also possible to select a fixed number y of pulses, the number y likewise being able to be regulated via the evaluation and control unit 80. A preferred number of pulses y is between 1 and 100, in particular 10, but it is, of course, dependent on the pulse repetition frequency chosen and/or the pulse length chosen.

If the radiation of the processing laser beam 20 onto the tooth 60 means that the plasma 30 ignites, which occurs only when the system is in a correct processing state, in particular, by way of example, a handpiece is held such that the surface of the tooth 60 on which the processing laser beam 20 impinges is in the desired depth of field range, then the plasma radiation 32 generated is detected by the optical detection device 70, and a corresponding signal 72 is generated and fed to the evaluation and control unit 80. Only if the signal 72 specifies, within the abovementioned time $t_2$ or the defined number y of pulses of the evaluation and control unit 80, that a plasma 30 is being generated does the evaluation and control unit 80 pass to the laser light source 10, by means of the control signal 82, the command to continue emitting a processing laser beam 20 as long as the activation device 100 is actuated by the treating physician.

For the case where no plasma is generated within the fixed time $t_2$ or in the defined number y of pulses and the optical detection device 70 therefore cannot detect plasma radiation, the evaluation and control unit 80 will generate a control signal 82 which puts the laser light source 10 into a quiescent mode, i.e. the laser light source 10 is switched off or shielded. Shielding may be performed by a shutter 14, which is designed such that it is integrated with the laser light source 10 in the embodiment shown in FIG. 1.

The method may proceed in a similar manner during continuous operation in which a plasma-induced ablation of the tooth material takes place. If the conditions change during ablation, for example if the treating physician holds the handpiece in such a way that the material to be processed is no longer in the depth of field range, then no plasma will be induced. The optical detection device detects this and forwards a corresponding signal 72 to the evaluation and control unit 80, which, either immediately or else, preferably, after a delay time $t_1$ or a defined number x of pulses, passes via a control signal 82 the command to switch off the laser light source 10, for example to shield it by means of the shutter 14, shielding being preferred since, particularly in the case of more complex laser light sources, the intention is to ensure that the latter run in uniform operation without interruptions.

If the laser light source 10 is now in a quiescent mode, for example because a plasma has not yet been ignited at the beginning of processing after the time period $t_2$ or after y pulses, or because an interruption of the plasma for a time period $t_1$ or for x pulses has been detected during the plasma-induced ablation, but at the same time the activation device 100 is still in its activated or actuated state, then it is possible, in one operating mode of the laser treatment apparatus, for the laser light source 10 to be automatically switched to the processing mode again by the evaluation and control unit 80 for example after a time period $t_3$ or after a defined number z of pulses. The method described above can then be carried out anew, i.e. it is possible to check, for example over a time period $t_2$ or over a number y of pulses, whether the plasma 30 is ignited again.

The methods described above may alternate and/or be repeated a number of times, but, in a preferred embodiment, the evaluation and control unit 80 is designed in such a way that, for example after a defined number of repetitions of the process of automatically putting the laser light source 10 into the processing mode, if no plasma is detected in the subsequent time period $t_1$, the laser light source 10 is then put into a quiescent mode, and a new cycle can be started for example merely through deactivation and renewed activation of the activation device 100, as has been described above.

In this embodiment, the evaluation and control unit 80 is configured such that it can be regulated, so that in particular desired parameters, in particular the desired time periods $t_1$, $t_2$, $t_3$ or the desired number x, y, z of pulses or else a desired number of repetitions of the individual cycles can be set, as explained above. The evaluation and control unit 80 can also be regulated to the effect that the signals 72 of the optical detection device 70 are selected in variable fashion, in particular fixed threshold values can be varied and fixed.

Usually, at least one threshold value is defined, the evaluation and control unit 80 assuming that no plasma is ignited if the signal 72 falls below said threshold value.

However, in the embodiment shown, the evaluation and control unit 80 is designed in such a way that a plurality of threshold values, in particular a first threshold value and a second threshold value, can be defined in variable fashion and stored, the evaluation and control unit 80 being designed in such a way that it switches the laser light source 10 from a processing mode to a quiescent mode if the signal 72 falls below a first threshold value, while it switches the laser light source 10 from a quiescent mode to a processing mode if the signal 72 of the optical detection device 70 exceeds a second threshold value, thereby realizing a hysteresis circuit.

Figure 2:
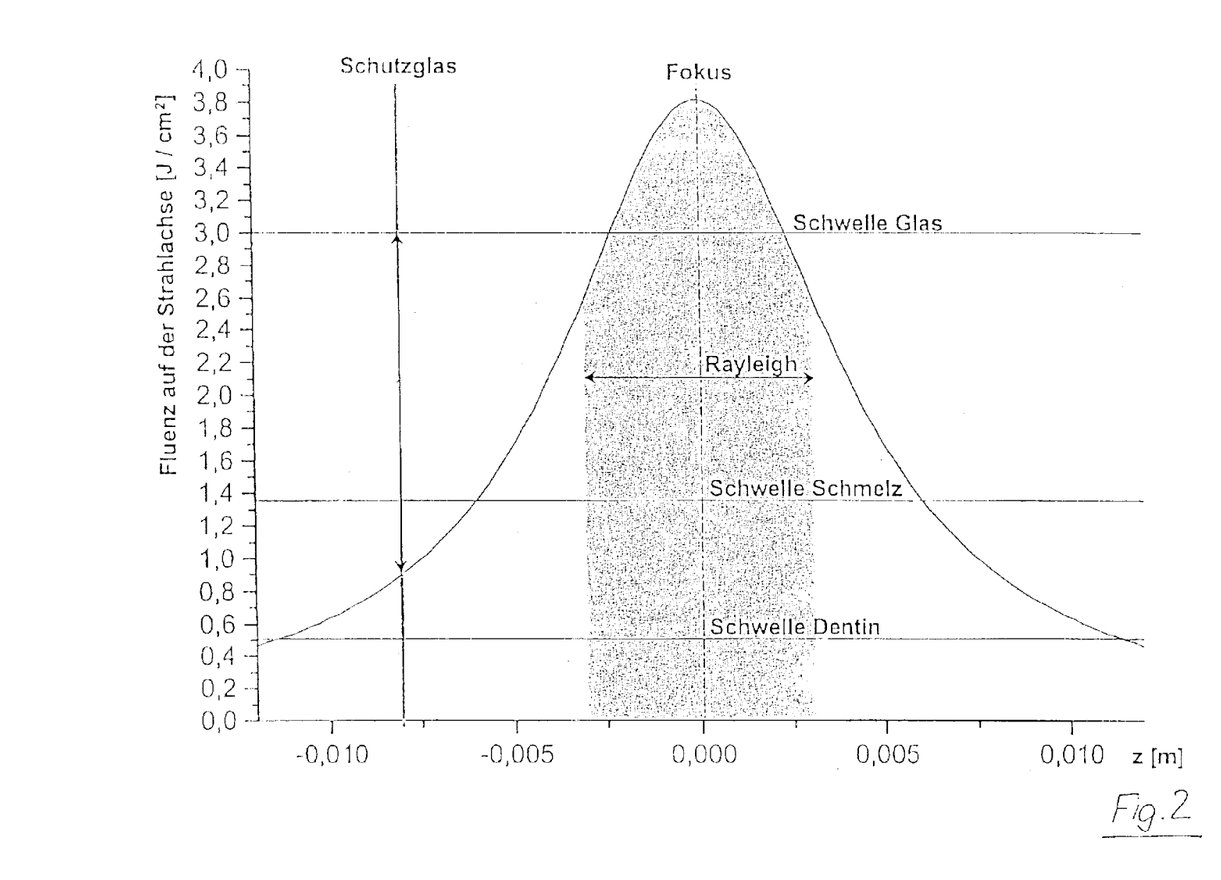
FIG. 2 shows a diagram illustrating the fluence of the processing laser beam as a function of the distance of the focal plane.

FIG. 2 shows a graph on which the fluence of a processing laser beam is illustrated as a function of the distance of the focus. This graph is based on a high-energy, pulsed processing laser beam, laser light having a wavelength of 780 nm being emitted. The processing laser beam has a focus diameter of 100 $\mu$m and emits a pulsed laser light having a pulse length of 700 fs, the laser pulses being emitted with a pulse frequency of 10 kHz. The emitted laser energy is 150 $\mu$J.

Depending on the material to be ablated, a plasma-induced ablation only starts from a certain minimum fluence, dentine ablating at as little as about 0.5 $J/cm^2$, and enamel only ablating starting from a fluence value of almost 1.4 $J/cm^2$. The corresponding ablation thresholds are illustrated in FIG. 2.

The ablation threshold of glass, which is about 3.0 $J/cm^2$, has also been illustrated for comparison purposes. The ablation threshold of glass is significant because when a handpiece is used, as described above, the processing laser beam (20, see FIG. 1) is radiated from a handpiece generally through a closing-off protective glass (110, see FIG. 1), which closes off the interior of the handpiece. Since this protective glass is situated in the vicinity of the focus, high fluences already occur, under certain circumstances, on the protective glass.

As can be gathered from FIG. 2, a protective glass is arranged at a distance of 8 mm from the focus, so that a fluence of about 0.9 $J/cm^2$ occurs at the protective glass. However, since an ablation of the protective glass only occurs starting from a fluence of approximately 3 $J/cm^2$, a safety factor of approximately 3.5 is provided for the protective glass (110, see FIG. 1).

In the case of a very high-energy, pulsed processing laser beam as is the basis of the diagram shown in FIG. 2, a plasma-induced ablation of enamel and dentine occurs even when the material to be processed is not situated exactly or in direct proximity to the focus. As can be seen from FIG. 2, a plasma-induced ablation of enamel occurs even when the material to be processed is situated at a distance of approximately ±6 mm from the focus, while a plasma-induced ablation of dentine occurs even when the material is situated at a distance of approximately ±12 mm from the focus.

Therefore, if tooth enamel, for example, is ablated or processed, a plasma occurs whenever the tooth enamel to be processed is at a distance of at most ±6 mm from the focus. As long as this range is complied with, ablation takes place and the laser processing apparatus is in an operating mode.

If, by way of example, a handpiece is then guided by a treating physician in such a way that the distance between the tooth enamel to be processing and the focus is more than ±6 mm, a fluence lying below the fluence threshold acts on the tooth enamel to be processed, so that no plasma-induced ablation takes place and no plasma is generated. In this case, the laser processing apparatus automatically switches the laser light source to a quiescent mode, as explained above. The ablation thresholds are material-dependent, so that very different ranges in which a plasma-induced ablation of the material to be processed takes place may result depending on the material to be processed and depending on the power of the laser light source. By way of example, if a weaker laser light source is used, the fluence curve in FIG. 2 would be shifted downward, so that the regions in which a plasma-induced ablation takes place diminish, thus necessitating more accurate positioning of, for example, a handpiece.

Figure 3:
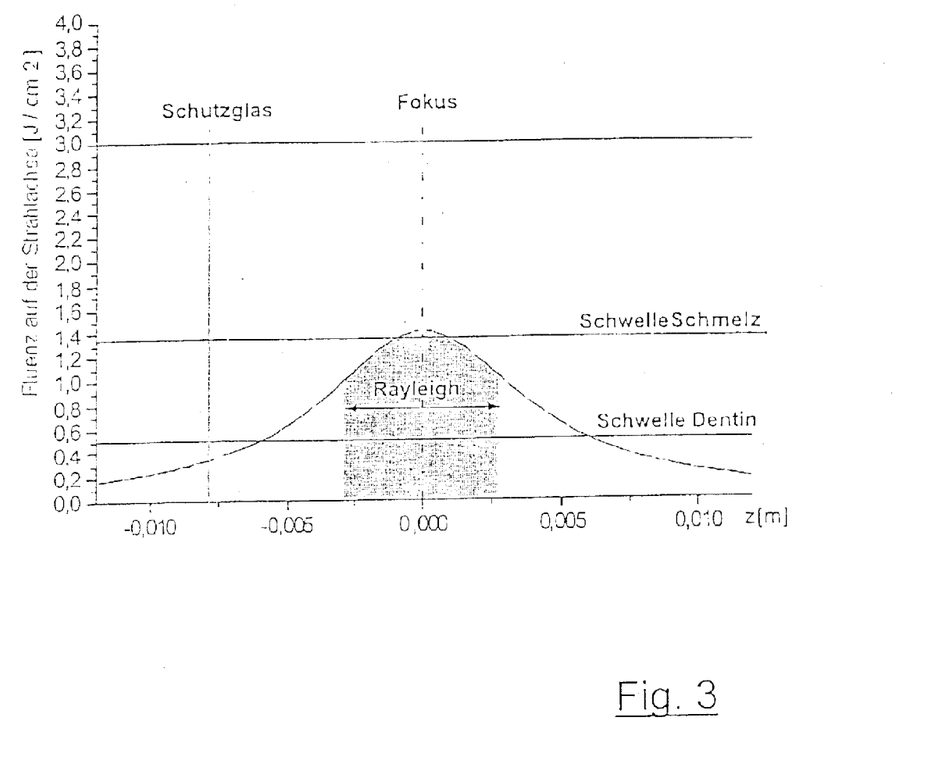
FIG. 3 shows a diagram which is analogous to FIG. 2 but which is based on a lower-power processing laser beam.

FIG. 3 shows a diagram which is analogous to FIG. 2, but in which a laser light source having a lower power was used. As can be seen from the figure, the maximum fluence that can be achieved at the focus is approximately 1.4 $J/cm^2$, so that, in the case of such a laser light source, a plasma-induced ablation of tooth enamel occurs only when the material to be processed is situated at a distance of approximately ±1 mm from the focus, while a plasma-induced ablation of dentine occurs even when the material is situated at a distance of approximately ±6 mm from the focus.

Therefore, in the case of a laser light source of the kind on which the diagram of FIG. 3 is based, complying with the required distances from the material to be processed is significantly less critical than in the case of an embodiment with a laser light source on which the diagram from FIG. 2 is based.

In the case of the laser processing apparatus which led to the values for the fluence shown in FIG. 2, the protective glass is likewise situated 8 mm in front of the focus, and the relevant laser parameters are 56 µJ, 700 fs with a focus of 100 µm.

Figure 4:
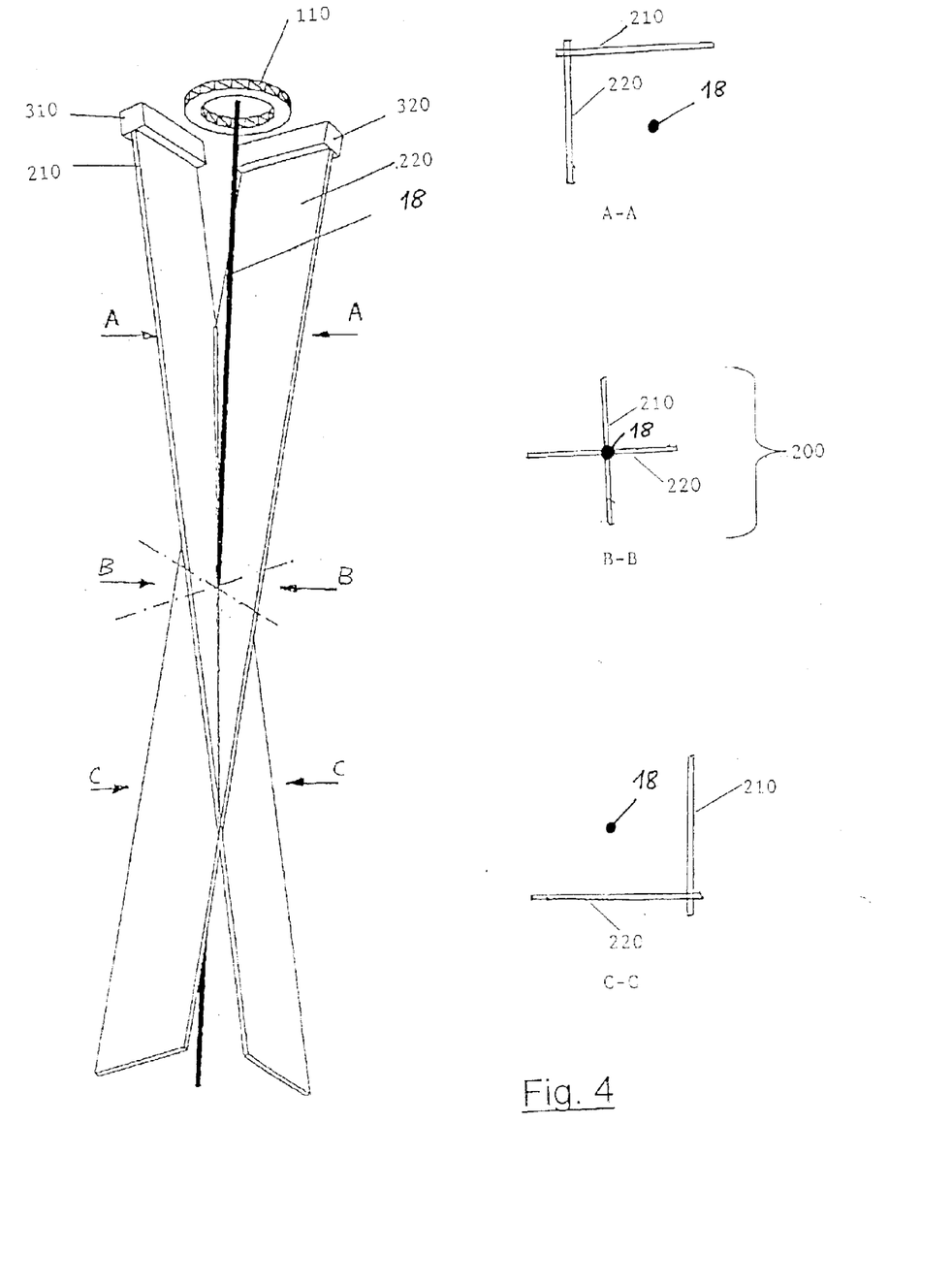
FIG. 4 shows an embodiment of a device for generating a distance indicator.

Finally, FIG. 4 schematically illustrates the principle of an optional device for generating a distance indicator. What is involved in the embodiment shown in FIG. 4 is a device for generating a light crosshair 200, which is formed by the superimposition of two light lines 210, 220. The light lines 210, 220 are generated by light sources 310, 320 arranged in such a way that the light lines 210 and 220 run obliquely with respect to one another and overlap in such a way that they form a uniform crosshair 200 at the focus, as is illustrated in the section B—B in FIG. 4.

Therefore, if the material to be processed is situated at the focus of the processing laser beam 20, which is only indicated schematically here, then a uniform crosshair formed from the light lines 210, 220 is therefore visible on the material to be processed.

If the area to be processed or the material to be processed is situated for example too close to a handpiece, that is to say between focus and laser light source or between focus and a protective glass 110—illustrated schematically here—of a handpiece, or too far away, that is to say behind the focus, then the projected light lines 210 and 220 move apart, as is shown in the sectional illustration A—A and in the sectional illustration C—C in FIG. 4.

Therefore, such a distance indicator device provides the operator of a laser processing apparatus with an indicator of whether, for example, he is holding a handpiece in such a way that the region to be processed is situated essentially at the focus of the processing laser beam or else outside the focus. Such a device is a highly advantageous optional supplementation to a laser processing apparatus according to the invention and assists convenient operation of the apparatus.

In conjunction with a pilot laser, which may likewise optionally be provided and which generates a pilot laser beam 18, the indicator device becomes even more advantageous for the user. As is likewise shown in FIG. 4, the light spot generated by the pilot laser beam 18 is furthermore visible to the user in addition to the light lines 210 and 220 on the area to be processed or the material to be processed, as can be seen in particular in the sectional illustrations A—A, B—B and C—C in FIG. 4.

In the case of the "ideal positioning", therefore, as shown in the sectional illustration B—B, the point of intersection of the crosshair exactly overlaps the light spot of the pilot laser beam 18, so that even possibly very slight displacements of the light lines 210 and 220 become clear to the user on account of the relative positioning with respect to the light spot generated by the pilot laser beam 18.

A combination of an optional distance indicator device with the—likewise optional—pilot laser therefore provides the user with the possibility of a particularly advantageous and effective aid for the handling and correct positioning of, for example, a handpiece or angle member.

The features disclosed in the above description, the claims and the drawing may be of importance both individually and in any desired combination for the realization of the invention in its various configurations.

What is claimed is:

1. A laser processing apparatus for plasma-induced ablation having a laser light source for generating a processing laser beam;

a focusing means for focusing the processing laser beam; and an optical detection device for detecting plasma radiation generated during an ablation, wherein, the laser processing apparatus comprises an evaluation and/or control unit and the optical detection device outputs to the evaluation and/or control unit, a signal dependent on the intensity of the detected plasma radiation, and the laser processing apparatus is automatically switched form a processing mode into a quiescent mode and/or from the quiescent mode into the processing mode, in a manner dependent from said signal.

2. The laser processing apparatus as claimed in claim 1, wherein said apparatus is automatically switched from a processing mode into a quiescent mode if the intensity of the plasma radiation detected by the optical detection device at a specific measurement time falls below a definable first threshold value.

3. The laser processing apparatus as claimed in claim 1, wherein the quiescent mode comprises a temporally restricted trial mode during which a processing laser beam is emitted and the laser processing apparatus is automatically switched into a processing mode if the intensity of the plasma radiation detected by the optical detection device at a specific measurement time rises above a definable second threshold value on account of the processing laser beam emitted in the trial mode.

4. The laser processing apparatus as claimed in claim 1, wherein the laser processing apparatus furthermore comprises an activation device which can be actuated by a user wherein the laser processing apparatus is in the quiescent mode if it is not actuated by the user.

5. The laser processing apparatus as claimed in claim 1, further comprising a delay device.

6. The laser processing apparatus as darned in claim 1, wherein the threshold value or values and/or the fluence of the processing laser beam are adjustable.

7. The laser processing apparatus as claimed in claim 1, further comprising a synchronizing device which adapts the optical detection device and/or the evaluation and/or control unit to the radiation characteristic of the laser light source.

8. The laser processing apparatus as claimed in claim 7, wherein the laser light source emits a pulsed processing laser beam and the synchronizing device adapts the optical detection device and/or the evaluation and/or control unit to a pulse repetition rate f of the processing laser beam in such a way that the detected intensity of the plasma radiation is used with a corresponding detection repetition rate f for controlling the medical laser processing apparatus.

9. The laser processing apparatus as claimed in claim 8, wherein the laser light source and the synchronizing device evaluate the intensity of the plasma radiation as a maximum in the time periods in which a laser light source working in pulsed operation emits a laser pulse with a pulse duration t.

10. The laser processing apparatus as claimed in claim 1, wherein it further comprises a device for generating a pilot laser beam.

11. The laser processing apparatus as claimed in claim 1, wherein it further comprises a device for optical, acoustic and/or tactile indication of the mode of the laser processing apparatus.

12. The laser processing apparatus as claimed in claim 1, wherein it further comprises a device for generating a distance indicator.

13. The laser processing apparatus as claimed in claim 12, wherein the device for generating a distance indicator comprises a projection device for projecting a crosshair in the focal plane of the processing laser beam.

* * * * *